United States Patent [19]

Neuzil et al.

[11] Patent Number: 4,886,929

[45] Date of Patent: Dec. 12, 1989

[54] SEPARATION OF PARA-XYLENE

[75] Inventors: Richard W. Neuzil, Downers Grove; George J. Antos, Bartlett, both of Ill.

[73] Assignee: UOP Inc., Des Plaines, Ill.

[21] Appl. No.: 61,948

[22] Filed: Jun. 15, 1987

[51] Int. Cl.$^4$ ............................ C07C 7/12; C07C 7/13
[52] U.S. Cl. .................................. 585/828; 585/820; 208/307
[58] Field of Search ..................... 200/310.7; 585/828, 585/820, 825

[56] References Cited

U.S. PATENT DOCUMENTS

| | | | |
|---|---|---|---|
| 2,985,589 | 5/1961 | Broughton | 210/34 |
| 3,201,491 | 8/1965 | Stine et al. | 260/676 |
| 3,558,732 | 1/1971 | Neuzil | 260/674 |
| 3,626,020 | 12/1971 | Neuzil | 260/674 SA |
| 3,663,638 | 5/1972 | Neuzil | 260/674 SA |
| 3,665,046 | 5/1972 | DeRosset | 260/674 SA |
| 3,668,266 | 6/1972 | Chen et al. | 260/674 |
| 3,686,342 | 8/1972 | Neuzl | 208/310 Z |
| 3,700,744 | 10/1972 | Berger et al. | 260/668 A |
| 3,707,550 | 12/1972 | Stine et al. | 260/674 SA |
| 3,734,974 | 5/1973 | Neuzil | 260/674 SA |
| 3,843,518 | 10/1974 | Magee et al. | 585/825 |
| 3,878,127 | 4/1975 | Rosback | 252/455 Z |
| 3,878,129 | 4/1975 | Rosback | 252/455 Z |
| 3,894,109 | 7/1975 | Rosback | 208/310 Z |
| 3,996,306 | 12/1976 | Korovs et al. | 208/30 Z |
| 3,997,620 | 12/1976 | Neuzil | 260/674 SA |
| 4,014,949 | 3/1977 | Hedge | 260/674 SA |
| 4,051,192 | 9/1977 | Neuzil et al. | 208/310 Z |
| 4,159,284 | 6/1979 | Seko et al. | 208/310 Z |
| 4,255,607 | 3/1981 | Miyake et al. | 585/825 X |
| 4,584,424 | 4/1986 | Barthomeuf | 585/828 |

FOREIGN PATENT DOCUMENTS 515562 6/1962 Japan.
009093 11/1979 Japan.

*Primary Examiner*—Glenn Caldarola
*Attorney, Agent, or Firm*—Thomas K. McBride; John F. Spears, Jr.; Jack H. Hall

[57] ABSTRACT

The separation of the para-isomer of a dialkyl benzene from a mixture of the isomers thereof, especially p-xylene, by contacting the mixture at adsorption conditions with a type X or type Y zeolite adsorbent, ion exchanged with barium and potassium, and recovering the para-alkylbenzene from the adsorbent by contacting the adsorbent with fluorobenzene or a difluorobenzene at desorption conditions.

19 Claims, 12 Drawing Sheets

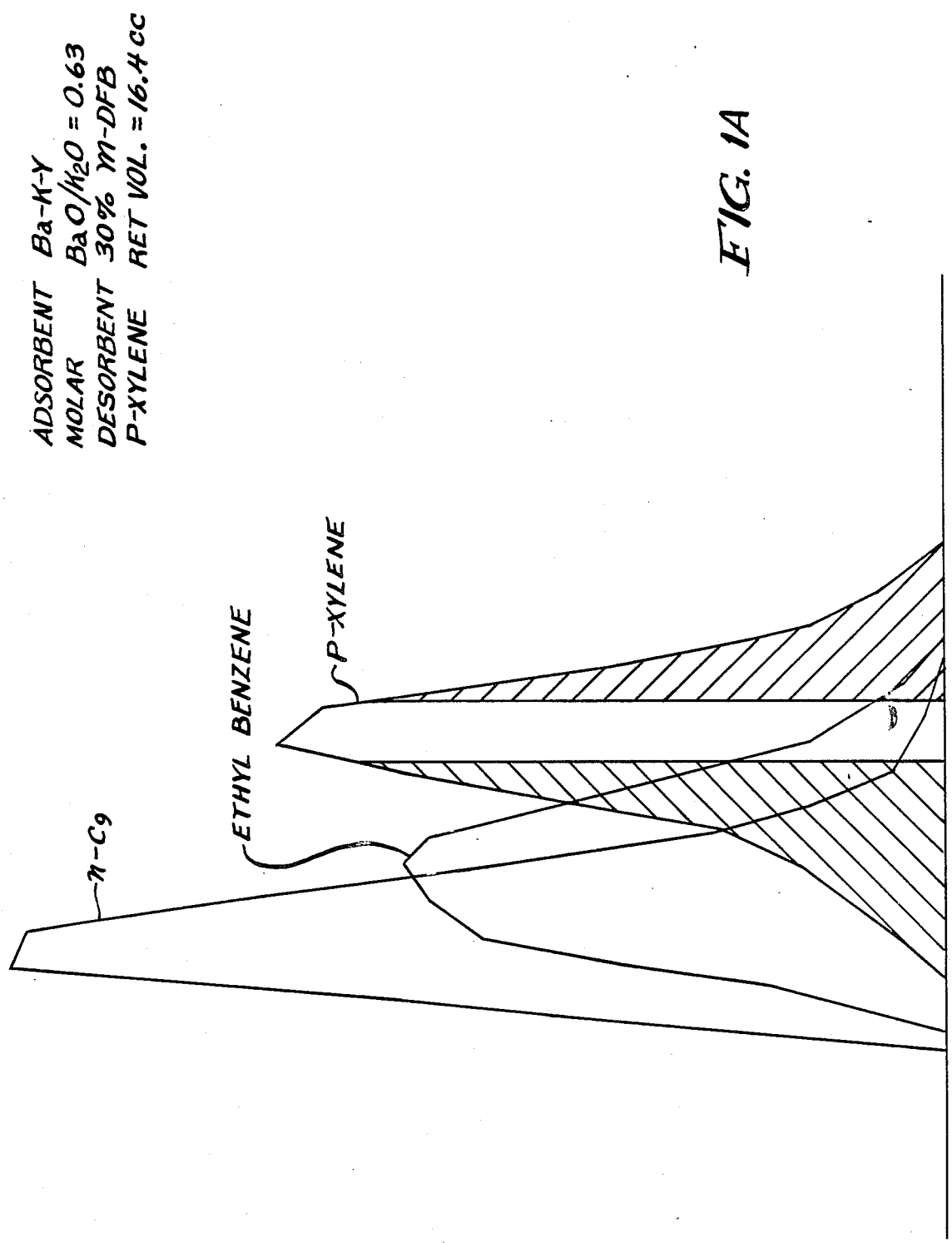

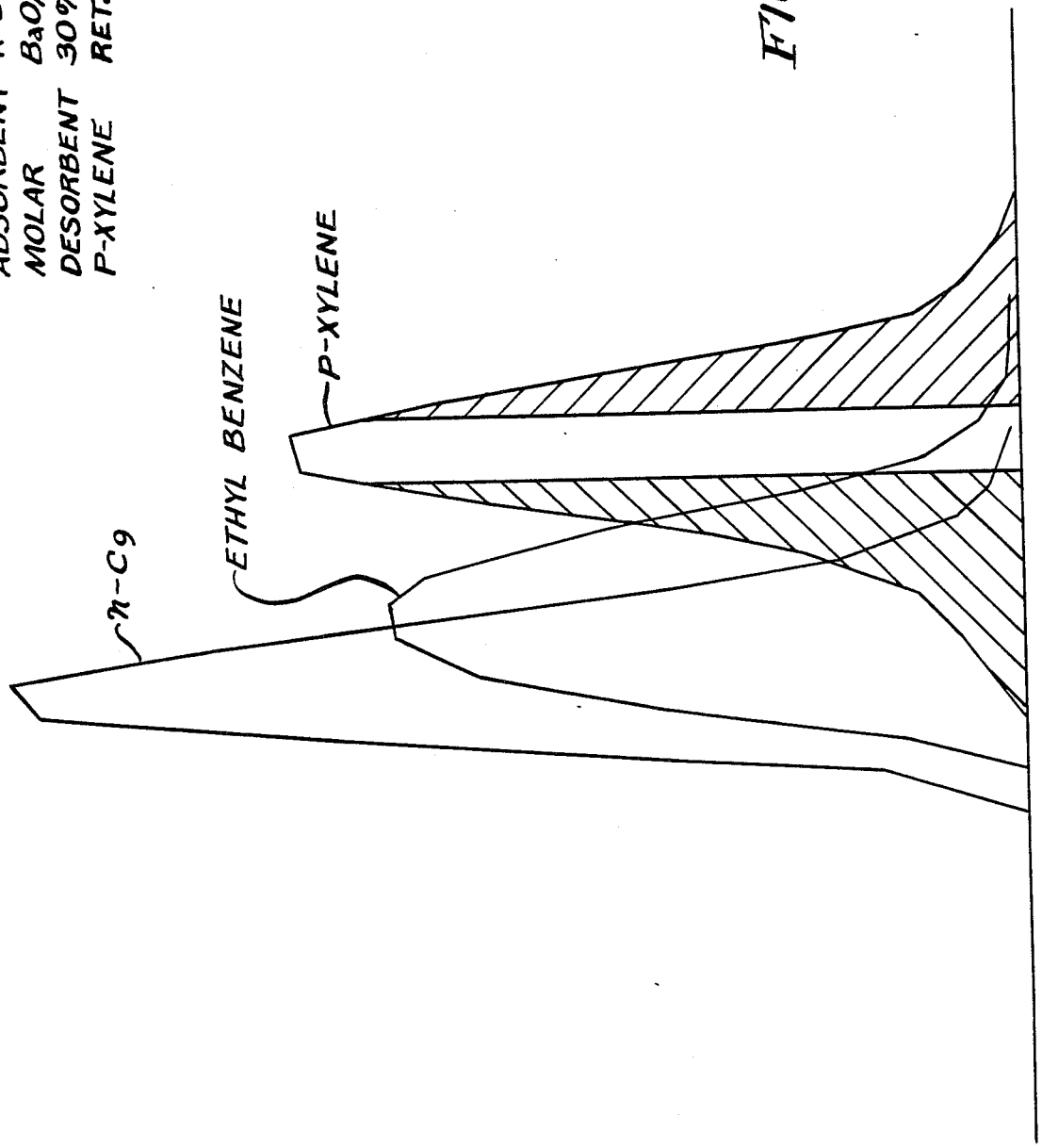

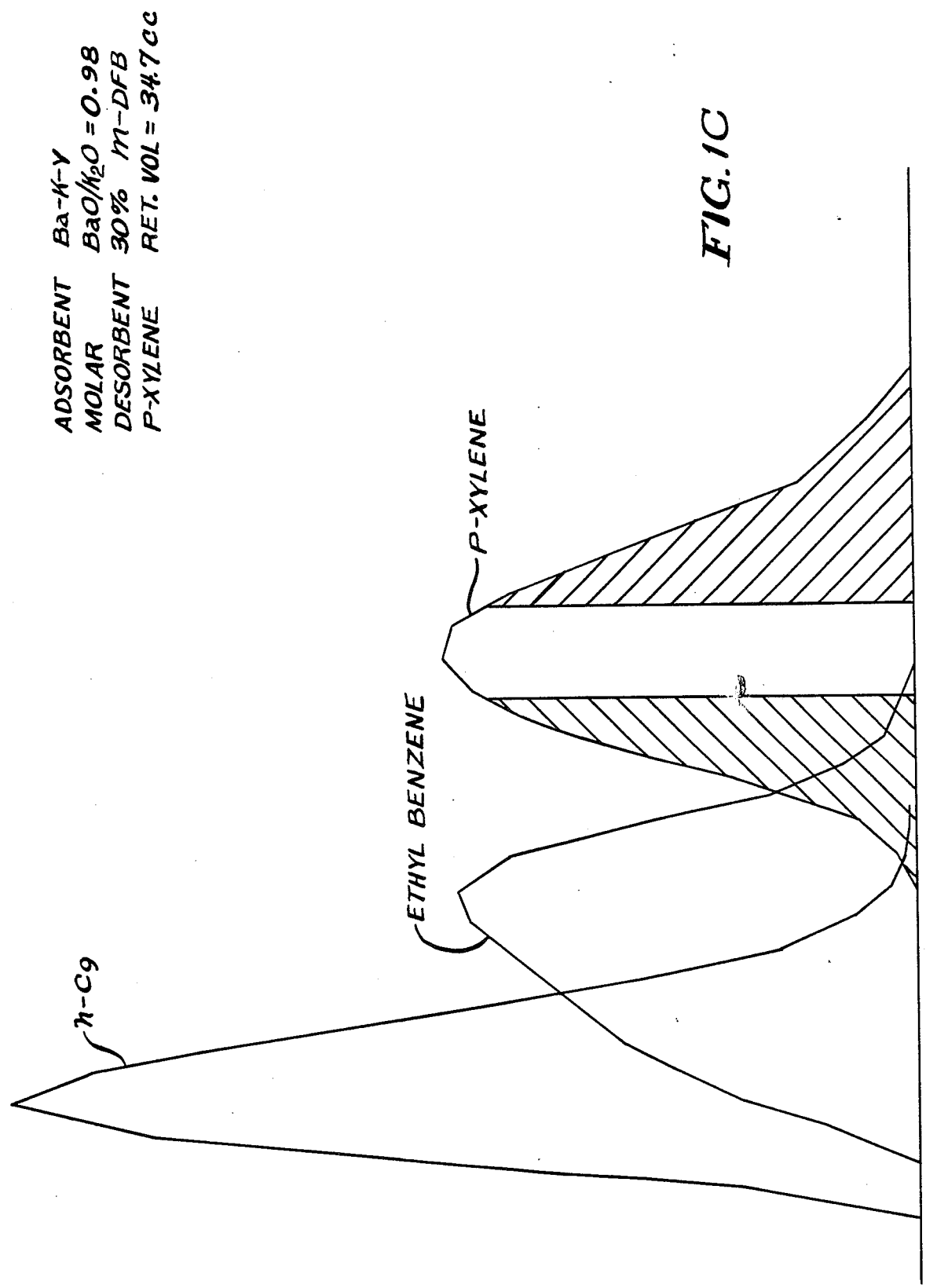

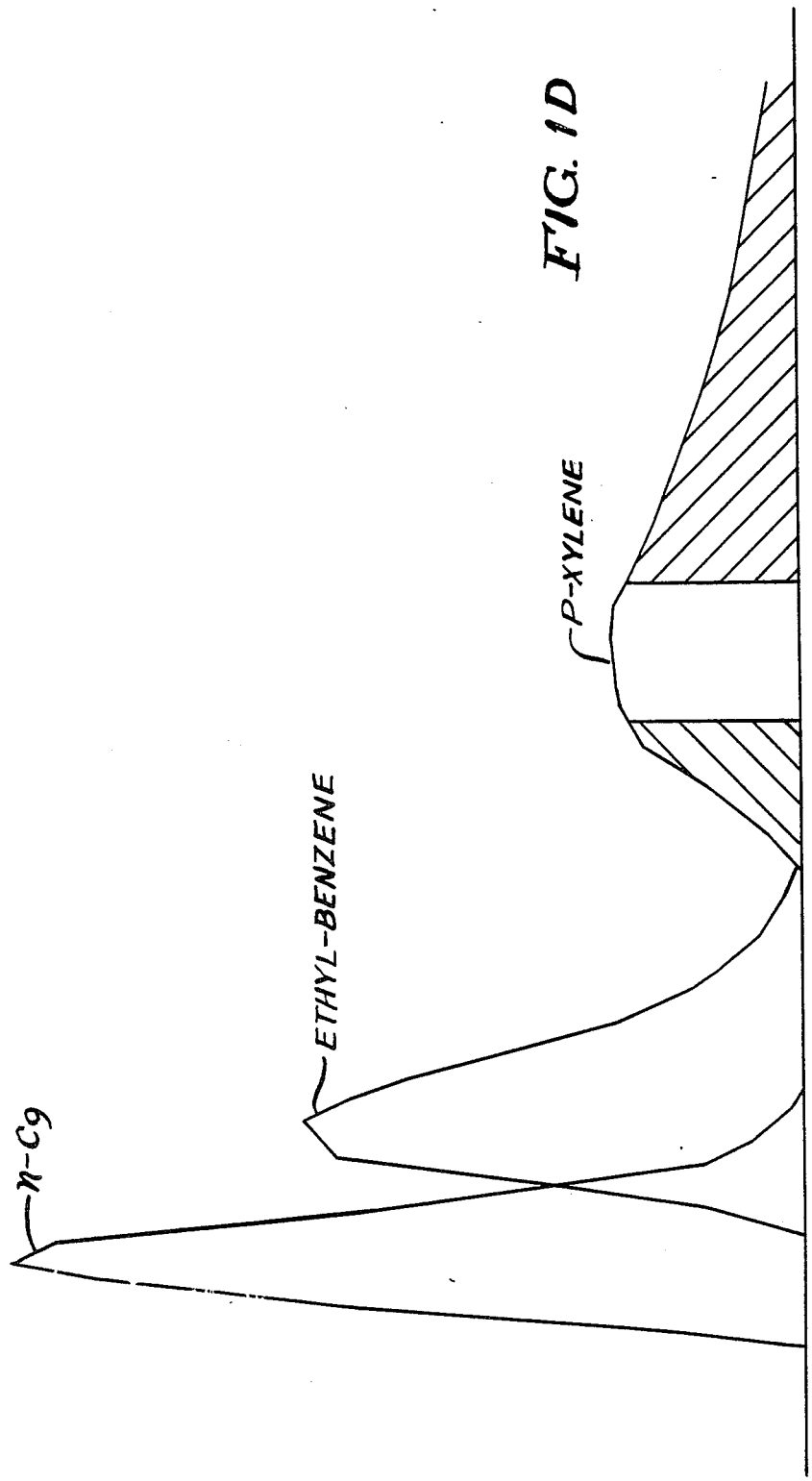

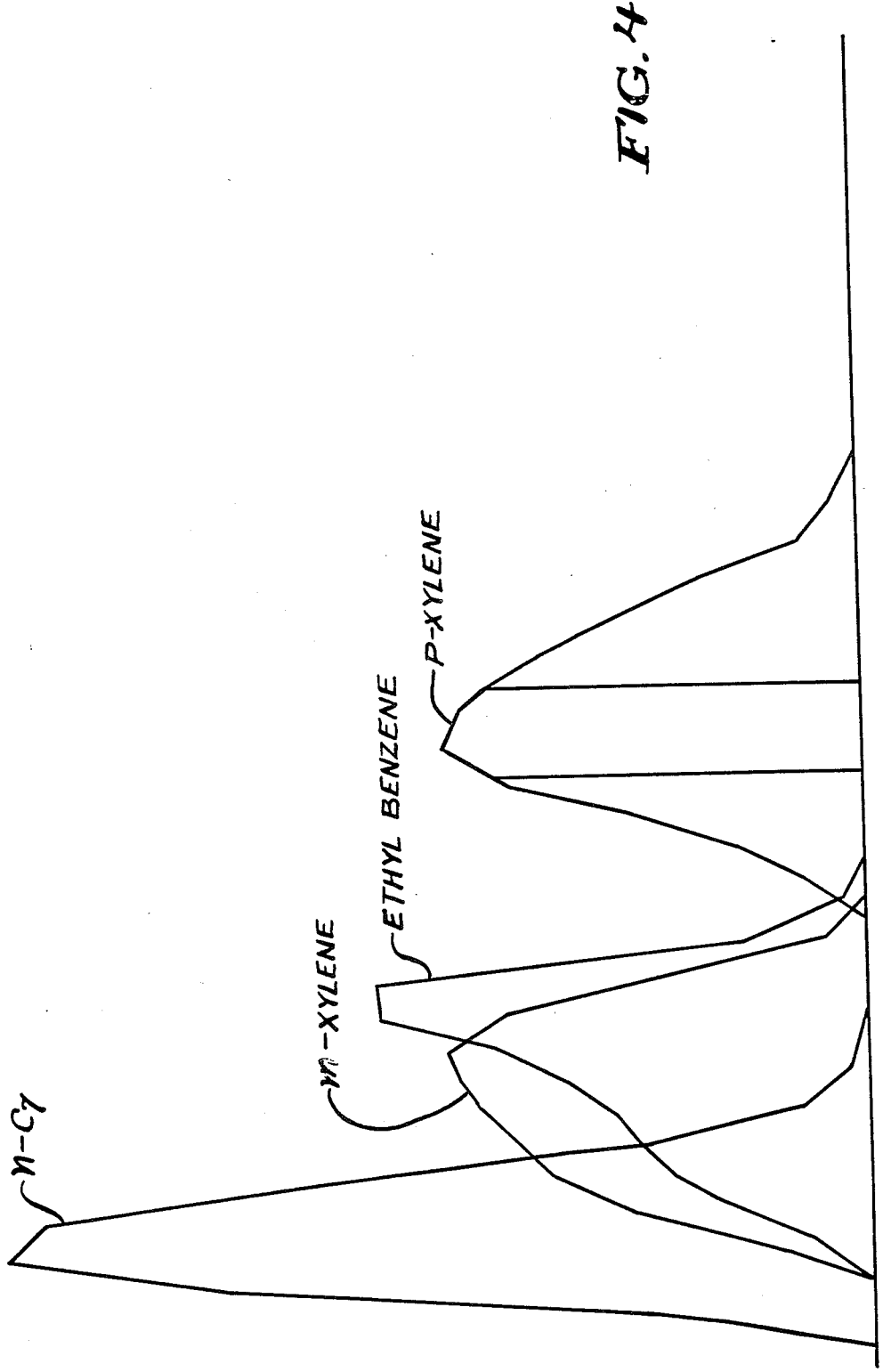

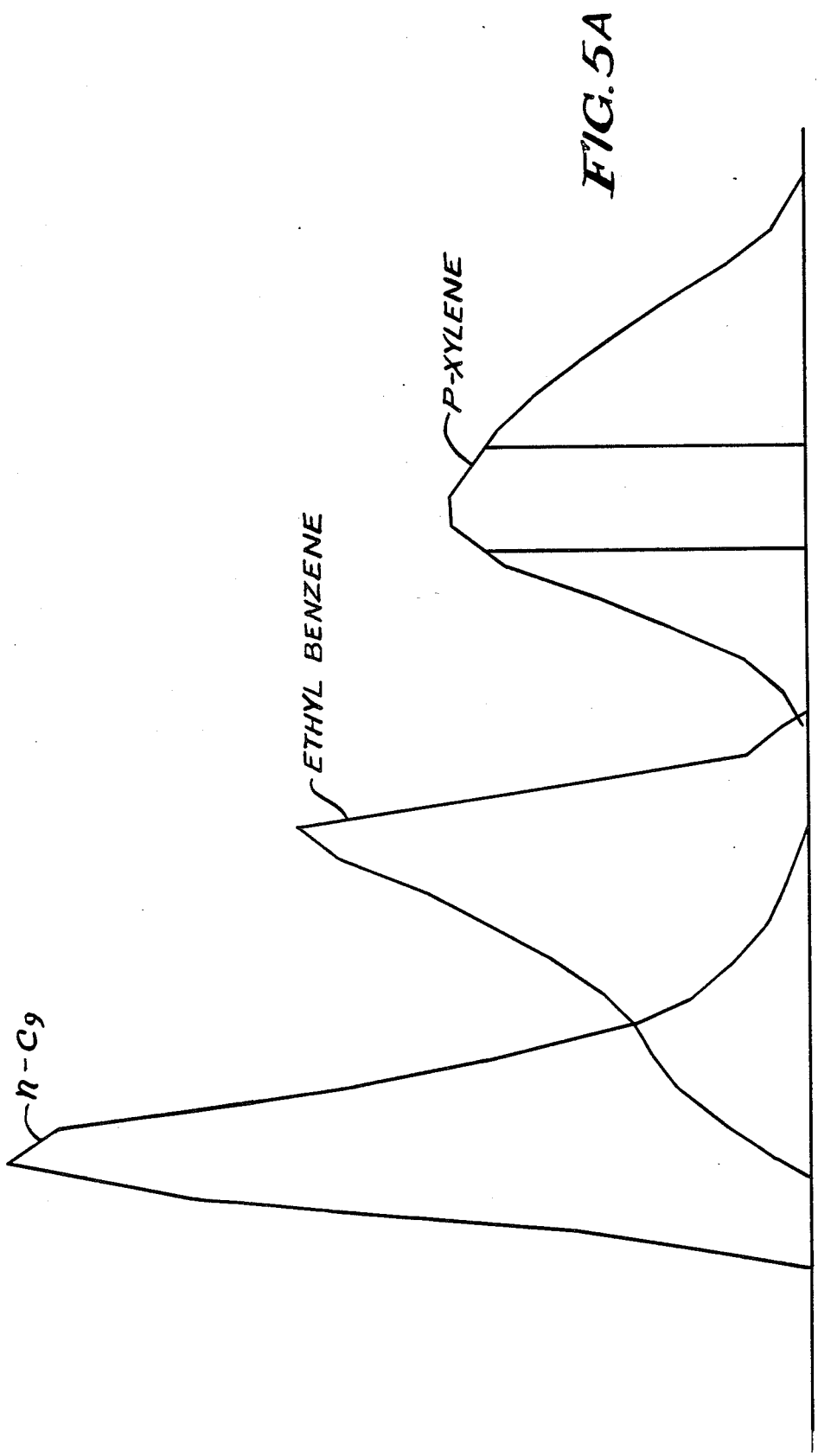

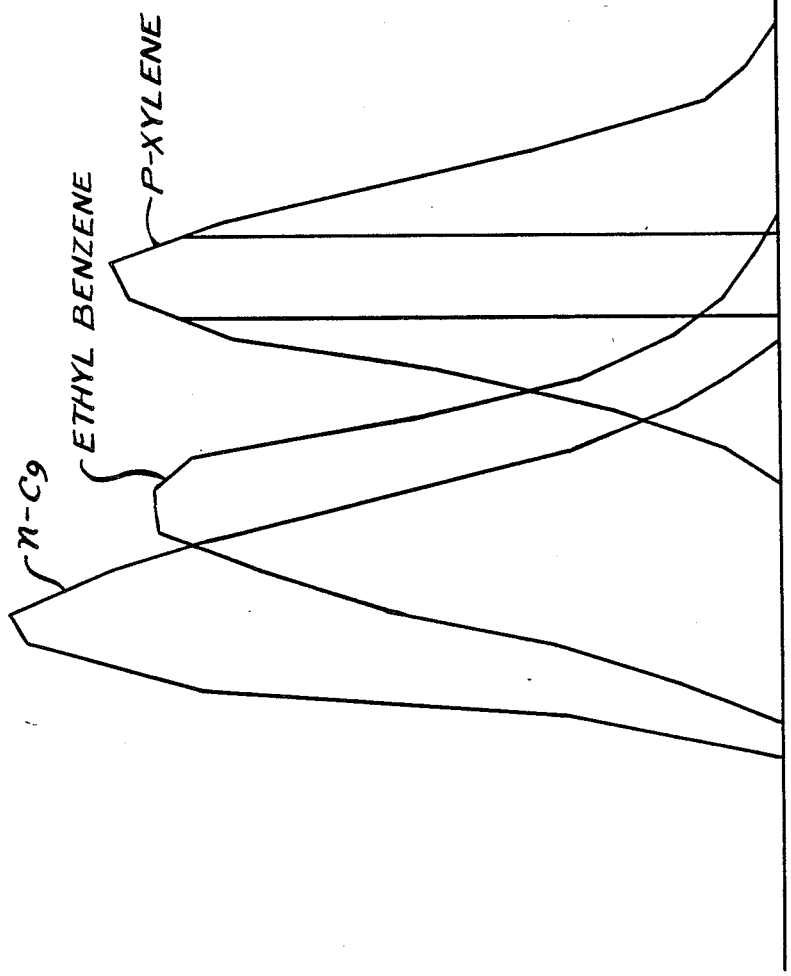

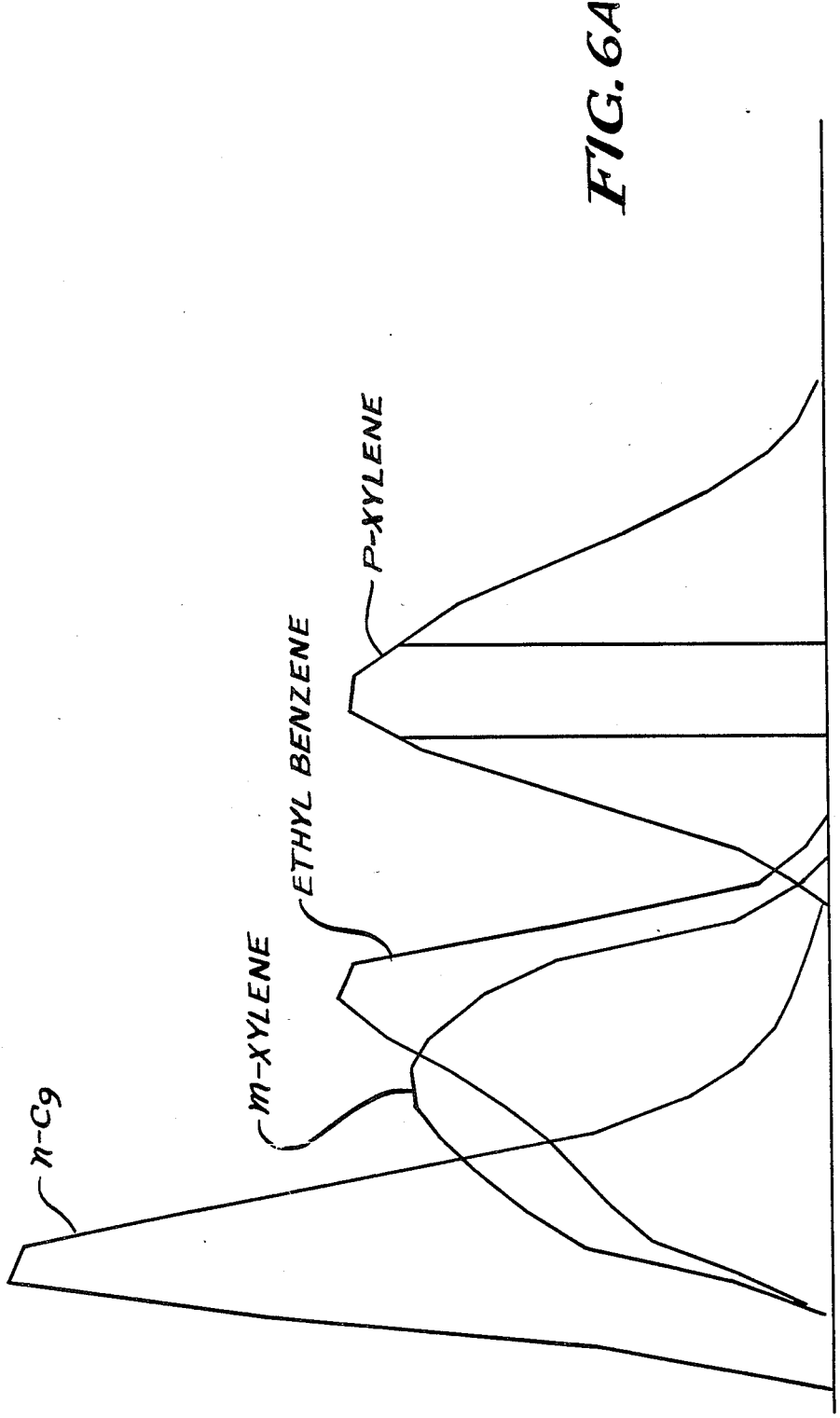

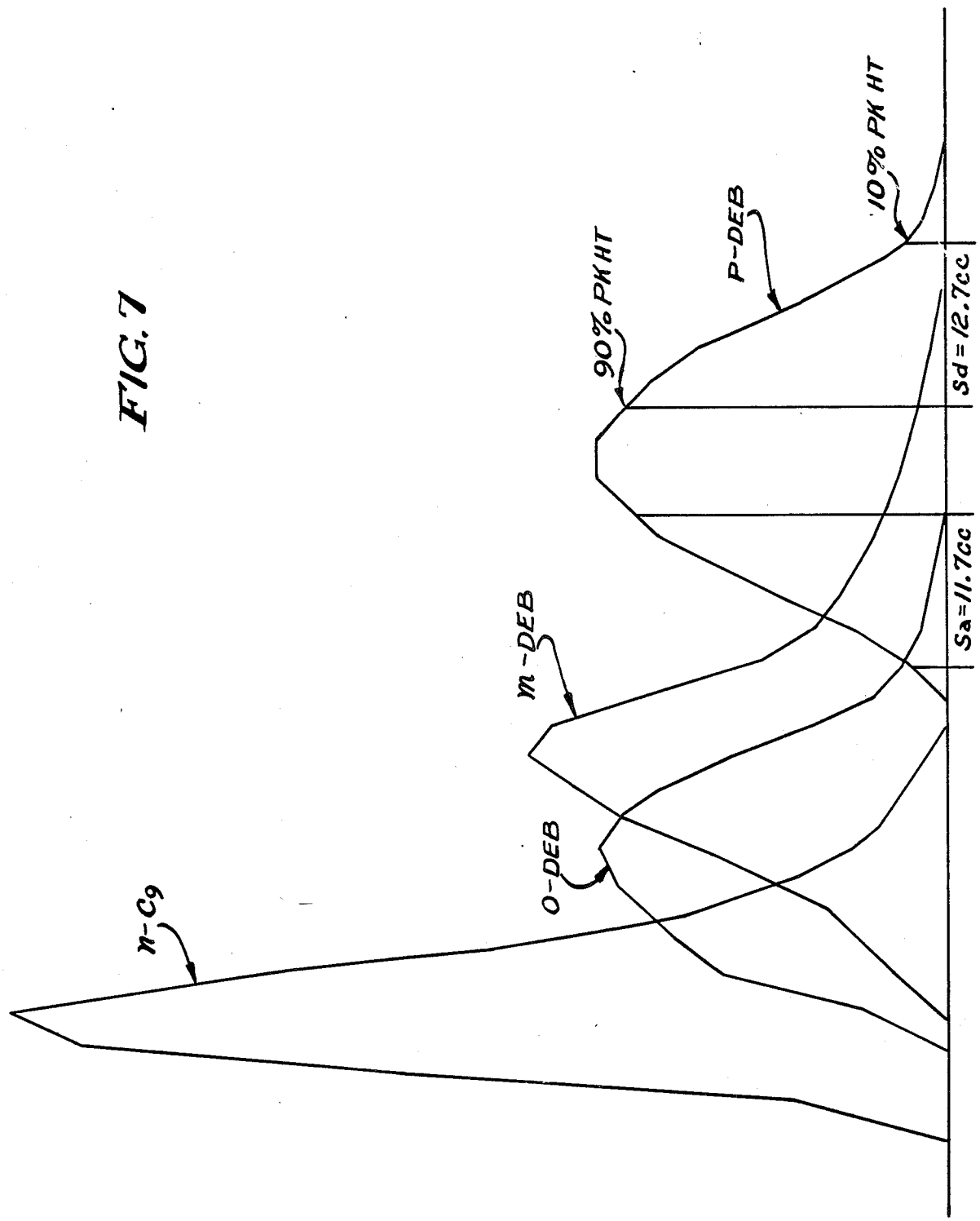

SEPARATION OF PARA-XYLENE

The field of art to which the claimed invention pertains is hydrocarbon separation. More specifically, the invention relates to a process for separating a dialkyl-substituted aromatic para-isomer from a feed mixture comprising at least two isomers thereof, particularly illustrated by separating para-xylene from a feed mixture comprising at least two isomers of said aromatic para-isomer, including the para-isomer, which process employs a particular zeolitic adsorbent and certain fluoro benzenes as desorbent and requires a certain class of desorbents to be used.

BACKGROUND OF THE INVENTION

It is well known in the separation art that certain crystalline aluminosilicates can be used to separate one hydrocarbon type from another hydrocarbon type. The separation of normal paraffins from branched chain paraffins, for example, can be accomplished by using a type A zeolite which has pore openings from 3 to about 5 angstroms (Å). Such a separation process is disclosed in U.S. Pat. Nos. 2,985,589 to Broughton et al. and 3,201,491 to Stine. These adsorbents allow a separation based on the physical size differences in the molecules by allowing the smaller or normal hydrocarbons to be passed into the cavities within the zeolitic adsorbent, while excluding the larger or branched-chain molecules.

In addition to being used in processes for separating hydrocarbon types, adsorbents comprising type X or Y zeolites have also been employed in processes to separate individual hydrocarbon isomers. In the processes described, for example in U.S. Pat. Nos. 3,626,020 to Neuzil, 3,663,638 to Neuzil, 3,665,046 to de Rosset, 3,668,266 to Chen et al., 3,686,342 to Neuzil et al., 3,700,744 to Berger et al., 3,734,974 to Neuzil, 3,894,109 to Rosback, 3,997,620 to Neuzil and B426,274 to Hedge, particular zeolitic adsorbents are used to separate the para-isomer of bialkyl substituted monocyclic aromatics from the other isomers, particularly para-xylene from other xylene isomers. U.S. Pat. No. 3,707,550 to Stine et al. mentions (as one possibility among a very large group), a silver or silver/potassium exchanged X-zeolite for use in the separation of $C_8$ aromatic isomers, but only following the removal of the ortho-xylene in a "separation zone" by means which appear to be conventional distillation.

Many of the above patents use benzene, toluene or p-diethylbnnzene as the desorbent. It has been previously recognized that benzene has drawbacks when used as a lower boiling desorbent in contact with the adsorbent (3,686,342 - Neuzil). Toluene suffers in the process for separating isomers of xylene, in recovering desorbent from the extract and raffinate, because the boiling point of the toluene is too close to the isomers being separated. Therefore, an even lower boiling point material, that meets the selectivity requirements for desorbents discussed herein, is desirable. Others of the patents listed above make reference to separation of para-xylene from other isomers of xylene with a zeolite exchanged with barium and potassium in a certain weight ratio. See for example U.S. Pat. Nos. 3,663,638; 3,878,127; 3,878,129; 3,686,342 and 3,558,732. Japanese published Application No. 5155/62, filed Mar. 3, 1960 discloses the separation of aromatic isomers by adsorption on X type zeolites exchanged, for example, with a metal, such as barium, calcium, sodium, etc. Exchange fluids may be benzene, toluene, chlorobenzene, 1-fluoroalkane, $\alpha,\omega$-dihaloalkane, halogen-substituted benzene, halogen-substituted toluene, depending upon the feed mixture, e.g., benzene for xylenes and/or ethylbenzenes, toluene for trimethylbenzenes or ethyltoluenes, chlorobenzene for halogenated aromatic isomer mixture.

U.S. Pat. No. 4,584,424 to Barthomeuf discloses a process for separating ethylbenzene from xylenes by selective adsorption on a beta zeolite. Although para-diethylbenzene is the preferred desorbent for this separation, monohalobenzenes, particularly iodobenzenes, are discussed.

SUMMARY OF THE INVENTION

In brief summary the present invention is, in one embodiment, a process for separating a dialkyl-substituted aromatic para-isomer from a feed mixture comprising said dialkyl-substituted aromatic para-isomer and at least one other isomer thereof. In a preferred embodiment, para-xylene is separated from a feed mixture comprising para-xylene and at least one other xylene isomer or ethylbenzene. The process comprises contacting, at adsorption conditions, the feed with an adsorbent comprising an X-type or Y-type zeolite having Ba and K cations at exchangeable cationic sites within the adsorbent crystalline structure in a molar ratio of barium oxide to potassium oxide of about 0.6 to about 1.2, preferably, 0.9–1.1. The feed is then removed from the adsorbent and a concentrated stream of the para-isomer is recovered by desorption at desorption conditions with a desorbent material comprising a monofluoro- or difluoro-substituted aromatic hydrocarbon.

Other embodiments of the present invention encompass details about feed mixtures, flow schemes and operating conditions, all of which are hereinafter disclosed in the following discussion.

BRIEF DESCRIPTION OF THE DRAWINGS

FIG. 1A is a chromatographic representation of the separation of p-xylene from a mixture of xylene isomers and ethylbenzene with a Ba- and K-exchanged Y zeolite and meta-difluorobenzene. FIGS. 1B, C and D are similar to 1A at different conditions and concentrations. To simplify the results in this Figure and FIGS. 4, 5A, 5B and 6A, and for clarity, the traces for ortho- and meta-xylene are omitted. Otherwise, the results would be similar to FIGS. 2 and 3. The molar ratios of BaO to $K_2O$ in FIGS. 1A through 1D are 0.63, 0.71, 0.98 and 5.17, respectively.

FIG. 4 is similar to FIG. 1A except that the BaO/$K_2O$ ratio is 1.05 and the desorbent is 30% meta-difluorobenzene in n-heptane.

FIGS. 5A and 5B are similar to FIGS. 1C and 1D, respectively, except that the molar ratio, BaO/$K_2O$, is 1.13 for FIGS. 5A and 5B.

FIGS. 6A and 6B are similar to FIGS. 1C and 1D, respectively, except that the molar ratio, BaO/$K_2O$, for FIGS. 6A and 6B is 0.99.

FIG. 7 is similar to 1A except that the feed mixture to be separated is a mixture of diethylbenzene isomers and the molar BaO/$K_2O$ ratio is 0.99.

DESCRIPTION OF THE INVENTION

Figure 2:
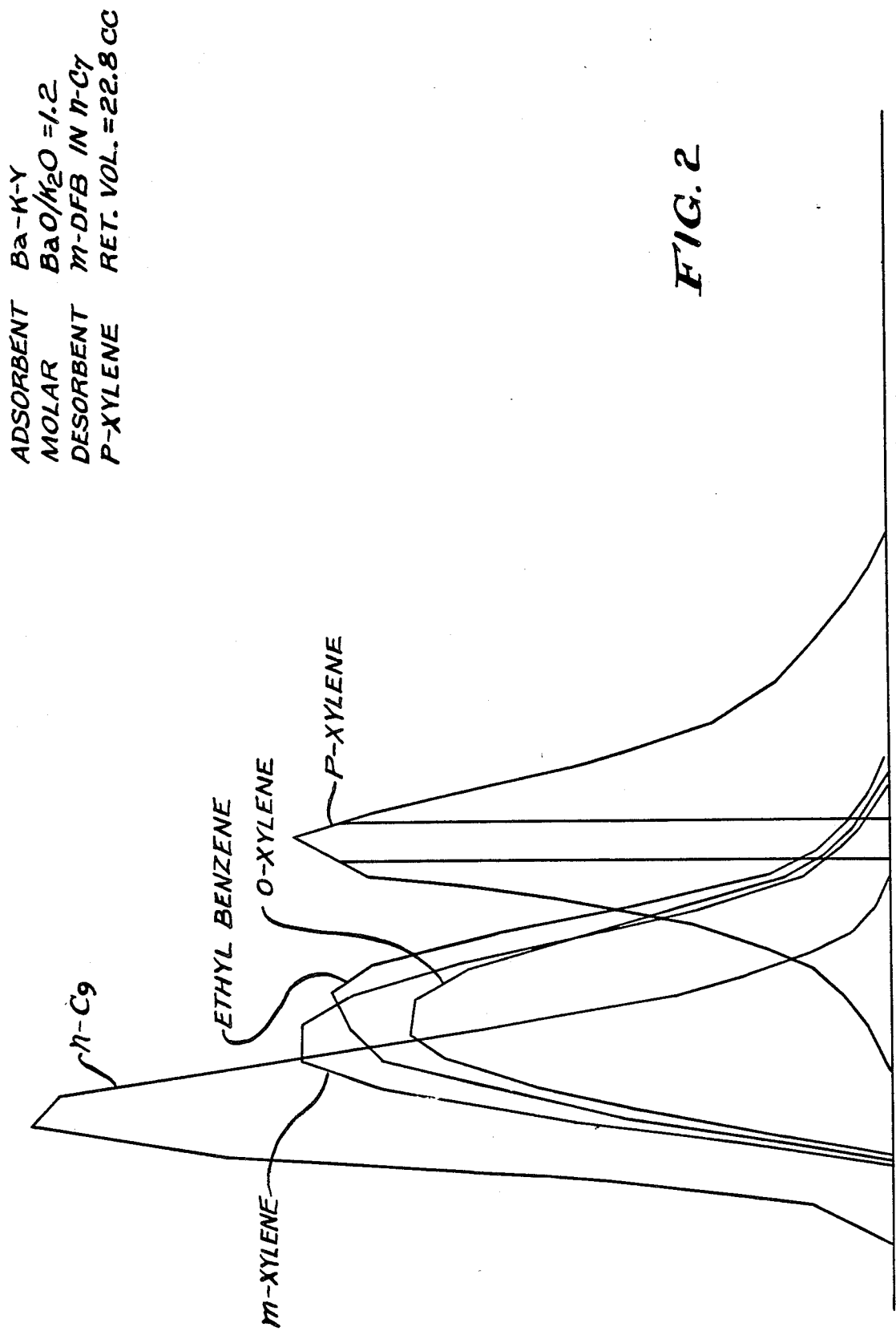
FIG. 2 is similar to FIG. 1A except that the molar ratio of BaO to $K_2O$ is 1.2. Also, all the isomers present are shown.

At the outset, the definitions of various terms used throughout this specification will be useful in making clear the operation, objects and advantages of the present invention.

A "feed mixture" is a mixture containing one or more extract components and one or more raffinate components to be fed to an adsorbent of our process. The term "feed stream" indicates a stream of feed mixture which passes to an adsorbent used in the process.

An "extract component" is a single compound or a class-type group of compounds such as aromatic isomers that is more selectively adsorbed by the adsorbent while a "raffinate component" is a compound or type of compounds that are less selectively adsorbed. In this process, the para-isomer of xylene is a single extract component and one or more other $C_8$ aromatics are the raffinate components. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely nonadsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed para-isomer to the concentration of less selectively adsorbed ortho-, meta-isomer or ethylbenzene, will be highest in the extract stream, next highest in the feed mixture, and lowest in the raffinate stream. Likewise, the ratio of the less selectively adsorbed meta- or ortho-isomers or the ethylbenzene to the more selectively adsorbed para-isomer will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "nonselective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the nonselective void volume are generally expressed in volumetric quantities and are of importance in determining the proper flow rates of fluid required to be passed into the process for efficient operations to take place for a given quantity of adsorbent.

Feed mixtures which can be utilized in the process of this invention will comprise a para-isomer of a $C_8$, $C_9$, $C_{10}$, $C_{11}$, or $C_{12}$ dialkyl-substituted aromatic composition and at least one other $C_8$–$C_{12}$ aromatic isomer thereof.

Included within the scope hereof are p-substituted benzenes, such as ethyl toluene ($C_9$), diethylbenzene ($C_{10}$), cymene (isopropyltoluene) ($C_{10}$), ethyl isopropylbenzene ($C_{11}$) and diisopropylbenzene ($C_{12}$).

Although many of the above p-substituted benzenes are available in quantities from alkylation processes, e.g., mixtures of cymene isomers produced by alkylation of toluene, other sources may also exist, and any such sources are intended as starting materials for our process. Mixtures containing substantial quantities of para-xylene and other $C_8$ aromatic isomers generally are produced by reforming and isomerization processes, processes which are well known to the refining and petrochemical arts. Also, known processes for making the isomeric compositions requiring separation are alkylation and dehydrocyclodimerization.

In reforming processes, a naphtha feed is contacted with a platinum-halogen-containing catalyst at severities selected to produce an effluent containing $C_8$ aromatic isomers. Generally, the reformate is then fractioned to concentrate the $C_8$ aromatic isomers in a $C_8$ fraction which will contain the $C_8$ aromatic isomers as well as $C_8$ nonaromatics.

Xylene isomerization processes isomerize a xylene mixture which is deficient in one or more isomers at isomerization conditions to produce an effluent containing approximately equilibrium quantities of the $C_8$ aromatic isomers as well as $C_8$ nonaromatics. The equilibrium compositions of the xylene isomers and ethylbenzene at various temperatures are shown in Table I below:

TABLE 1

| Equilibrium $C_8$ Aromatic Compositions | | | |
|---|---|---|---|
| Temperature, °C. | 327 | 427 | 527 |
| Mole percent of $C_8$ aromatic isomers | | | |
| Ethylbenzene | 6 | 8 | 11 |
| Para-xylene | 22 | 22 | 21 |
| Meta-xylene | 50 | 48 | 45 |
| Ortho-xylene | 22 | 22 | 23 |
| | 100 | 100 | 100 |

The feed mixtures may contain small quantities of straight or branched chain paraffins, cycloparaffins, or olefinic material. It is preferable to have these quantities at a minimum amount in order to prevent contamination of products from this process by materials which are not selectively adsorbed or separated by the adsorbent. Preferably, the above-mentioned contaminants should be less than about 20% of the volume of the feed mixture passed into the process.

To separate the para-xylene from a feed mixture containing para-xylene and at least one other $C_8$ aromatic, the mixture is contacted with the adsorbent and the para-xylene is more selectively adsorbed and retained by the adsorbent while the other components are relatively unadsorbed and are removed from the interstitial void spaces between the particles of adsorbent and the surface of the adsorbent. The adsorbent containing the more selectively adsorbed para-xylene is referred to as a "rich" adsorbent—rich in the more selectively adsorbed para-xylene. The para-xylene is then recovered from the rich adsorbent by contacting the rich adsorbent with a desorbent material.

To separate the para-isomers of the other feed materials set forth hereinabove, the same steps recited in the previous paragraph can be practiced to obtain an extract fraction containing predominantly the para-isomer. The desorption step mentioned in the paragraph below can be practiced in substantially the same manner with similar results.

The desorbent material may be a fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is, therefore, contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C., preferably 40° C. The boiling range of the desorbent material may be higher or lower than that of the feed mixture, but it is preferable that it be below, in the interest of economy of operation.

In the preferred isothermal, isobaric, liquid-phase operation of the process of this invention, it has been found that the effective desorbent material comprises monofluorobenzene or an ortho- or meta-difluorobenzene when the adsorbent is a barium and potassium cation exchanged X-type or Y-type zeolite, which has a ratio of barium oxide to potassium oxide of from 0.6 to 1.2, as hereinafter described. The ortho- and meta-difluorobenzenes of the invention are known compounds and may be prepared according to the literature, e.g., Kirk-Othmer, Vol. 10, 1980, pp. 909–14. The preparation of fluorobenzene is also well known, e.g., Kirk-Othmer, Vol. 9 (1966) pp. 781-3.

The prior art has recognized that certain characteristics of adsorbents are highly desirable, if not absolutely necessary, to the successful operation of a selective adsorption separation process. Among such characteristics are: adsorptive capacity for some volume of an extract component per volume of adsorbent; the selective adsorption of an extract component with respect to a raffinate component and the desorbent material; and sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component for a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another, but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases, respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally, desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rates, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze, "on-stream", the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed paraffinic tracer (n-nonane, for instance) and of the particular aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed isomer and the center of the peak envelope of the tracer component or some other known reference point. It is expressed in terms of the volume in cubic centimeters of desorbent pumped during this time interval. Selectivity, (B), may be expressed, for an extract component with respect to a raffinate component, by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the differences in widths of the $C_9$ (tracer) and p-xylene (adsorbed species) peak envelopes at half intensity (sometimes written herein as $\Delta W$). The narrower the peak width, the faster is the desorption rate. The desorption rate can also be characterized by the distance between the center of the tracer peak envelope and the disappearance of an extract component which has just been desorbed. This distance is, again, expressed as the volume of desorbent pumped during this time interval.

The adsorbent to be used in the process of this invention comprises a specific crystalline aluminosilicate. Crystalline aluminosilicates such as that encompassed by the present invention include crystalline aluminosilicate cage structures in which the alumina and silica tetrahedra are intimately connected in an open three-dimensional network. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction of the different isomers and the adsorbent rather than on pure physical size differences in the isomer molecules.

In hydrated form, the crystalline aluminosilicates generally encompass those zeolites represented by the Formula below:

$$M_{2/n}O:Al_2O_3:wSiO_2:yH_2O \qquad \text{Formula 1}$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are well known to the art.

The type X structured zeolite in the hydrated or partially hydrated form can be represented in terms of mole oxides as shown in Formula 2 below:

$$(0.9\pm0.2)M_{2/n}O:Al_2O_3:(2.5\pm0.5)SiO_2:yH_2O \qquad \text{Formula 2}$$

where "M" represents at least one cation having a valence of not more than 3, "n" represents the valence of "M", and "y" is a value up to about 9 depending upon the identity of "M" and the degree of hydration of the crystal. As noted from Formula 2, the $SiO_2/Al_2O_3$ mole ratio is $2.5\pm0.5$. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is, therefore, referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 3 below:

$$(0.9\pm0.2)M_{2/n}O:Al_2O_3:wSiO_2:yH_2O \qquad \text{Formula 3}$$

where "M" is at least one cation having a valence not more than 3, "n" represents the valence of "M", "w" is a value greater than about 3 up to 6, and "y" is a value up to about 9 depending upon the identity of "M", and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominantly sodium. The type Y zeolite containing predominately sodium cations at the exchangeable cationic sites is, therefore, referred to as a sodium type-Y zeolite.

The zeolites useful in the invention are typical as described above. However, the exchange of the cation of the as-manufactured zeolite by a mixture of barium and potassium ions in a particular range is necessary. Barium and potassium ions are exchanged in relative amounts so that the final molar ratio of $BaO/K_2O$ is from 0.6 to 1.2 and preferably is 0.9 to 1.1. The exchange can be in a single step with a mixture of Ba and K in a range of ratios such that the final zeolite will e in the abovementioned range or the exchanges may take place sequentially with each step exchanging an appropriate amount of ions to produce a zeolite in the correct and desired range. It has been found necessary to use a zeolite in the BaO/K₂O range mentioned above; otherwise, if the ratio is too great, the p-xylene retention volume becomes too high. The high retention volume indicates that desorption time will be long. If the ratio is below the specified range, the adsorbent becomes too selective for the desorbent and p-xylene will not effectively displace the desorbent on the next cycle.

Typically, adsorbents used in separative processes contain the crystalline material dispersed in an amorphous material or inorganic matrix, having channels and cavities therein which enable liquid access to the crystalline material. Silica, alumina or certain clays and mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh) (1.9 mm to 250 micron). Less water content in the adsorbent is advantageous in that it results in less water contamination of the product.

The adsorbent may be employed in the form of a dense fixed bed which is alternately contacted with a feed mixture and a desorbent material in which case the process will be only semicontinuous. In another embodiment, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a much greater separation efficiency than fixed bed systems and are, therefore, preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of the molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically, the concentration of desorbent material in the extract product and the raffinate product will be less than about 5 vol.% and more preferably less than about 1 vol.%. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vaporphase operation. Adsorption conditions will include a temperature range of from about 20° to about 250° C. with about 100° to about 200° C. being more preferred and a pressure sufficient to maintain liquid phase, which may be from about atmospheric to 600 psig. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour to many thousands of gallons per hour.

The following examples are presented for illustration purposes and more specifically, to illustrate the selectivity relationships that make the process of the invention possible. Reference to specific cations, desorbent materials, feed mixtures and operating conditions is not intended to unduly restrict the scope and spirit of the claims attached hereto.

EXAMPLE I

In this experiment, a pulse test, using the apparatus as described above, was performed to evaluate the ability of the present invention to separate para-xylene (b.p. 138° C.) from other $C_8$ aromatics (b p's. from 136°–145° C.). The adsorbent used was a Y faujasite exchanged with barium and potassium in the ratio indicated below. A small portion of an amorphous binder material comprising clay was used. The zeolite contained potassium or barium cations at substantially all the exchangeable cationic sites, the amount and ratio being given in the Table. The cation exchange was effected by passing 1.5 liters of 1 molar KCl solution at 50° C. upwards through a 200 cc bed of the adsorbent at 500 cc/hr. followed by recycling of a 0.2 M BaCl₂ solution over the bed for 4 hours at 1-liter /hr. and finally a water wash of 1 liter at 500 cc/hr. The adsorbent was calcined at 300° C.

For each pulse test, the column was maintained at a temperature of 150° C. and at a pressure of 150 psig so as to maintain liquid-phase operations. Gas chromatographic analysis equipment was attached to the column effluent stream in order to determine the composition of the effluent material at given time intervals. The feed mixture employed for each test contained about 5 vol. % each of the xylene isomers and ethylbenzene, 5 vol. % normal nonane which was used as a tracer and 75 vol. % desorbent material. The desorbent material for A, B, and C tests comprised 30 vol. % meta-difluorobenzene (m-DFB) with the remainder being n-C₇ paraffin. The desorbent material for Test D was 100% meta-difluorobenzene. The operations taking place for each test were as follows: The desorbent material was run continuously at a rate of about 1.20 cc per minute. At some convenient time interval, the desorbent was stopped and the feed mixture was run for 10 minutes at 1 cc/min. The desorbent stream was then resumed and continued to pass into the adsorbent column until all of the feed aromatics had been eluted from the column as determined by observing the chromatograph generated by the effluent material leaving the adsorption column.

The results of the tests are shown in Table 2 and the chromatographic tracings of FIGS. 1A, 1B and 1C and illustrate the invention. The para-xylene elution curves are clearly and distinctly separate from the other curves which is indicative of a good separation. FIG. 1D illustrates the separation, but is deemed impractical due to the long desorption time, indicating a decrease in desorption strength when the molar BaO/K₂O ratio increases. The molar BaO/K₂O ratio was 5.17. Relevant data calculated from the curves is as follows: $\Delta W$ (cc) is the difference in the widths of the peak envelopes of p-xylene and the n-C₉ tracer at half the heights of the peaks, and is a measure of the rate of exchange of the desorbent;

$$S_a\Big]_{10}^{90},$$

is the volume of para-xylene required to change the concentration of para-xylene in the effluent from 10% to 90% of its maximum concentration and is a measure of the rate of adsorption of para-xylene.

$$S_d\Big]_{10}^{90},$$

is the volume of desorbent required to change the concentration of p-xylene in the effluent from 90% to 10% of maximum and is a measure of the rate of desorption of the p-xylene. The volume required for the 10% to 90% change in $S_a$ is hereinafter referred to as the "adsorption breakthrough slope". The higher the value for $S_d$ or $S_a$, the slower the rate of desorption or adsorption, respectively. If the desorption slope, $$S_d\Big]_{10}^{90},$$

is steeper than the adsorption breakthrough slope, $$S_a\Big]_{10}^{90},$$

the selectivity of the adsorbent for p-xylene with respect to the desorbent is less than one and is unfavorable with respect to the adsorption process. An ideal system is one where the p-xylene/desorbent selectivity is just slightly greater than one and where the p-xylene peak envelope has a low retention volume. The p-xylene/desorbent selectivity can also be expressed as $S_d/S_a$ ratio.

Thus, using the data in Table II, for Examples 1C and 1A and 1B, $$B = S_d\Big]_{10}^{90} cc / S_a\Big]_{10}^{90} cc$$

$$B_{1C} = \frac{14.5}{10.8} = 1.34$$

$$B_{1A} = \frac{8.0}{14.6} = 0.55$$

$$B_{1B} = 0.76$$

Thus, the selectivity of the adsorbent of Example 1C for p-xylene is quite advantageous, while the desorbent selectivity of 1A and 1B tend to be unfavorable. Another trend noticed in the data of this example is that the adsorbent becomes weaker, (i.e., retention volume increases) with an increasing barium oxide/potassium oxide ratio.

TABLE 2

| PULSE TEST RESULTS FOR Ba—K—Y FAUJASITES AT VARIOUS Ba/K RATIOS | | | | |
|---|---|---|---|---|
| Example I | 1A | 1B | 1C | 1D |
| Desorbent | 30% m-DFB | | | 100% m-DFB |
| n-C₉ Half Width (H.W.) | 11.5 | 9.94 | 12.3 | 12.9 |
| Selectivity (B) | | | | |
| B p/eb | 3.27 | 3.53 | 3.32 | 4.64 |
| B p/m | 4.04 | 4.47 | 4.13 | 5.22 |
| B p/o | 3.40 | 3.64 | 3.56 | 5.16 |
| P—Xyl Ret. Vol. cc | 16.4 | 17.0 | 34.7 | 78.9 |
| $\Delta W$ cc | 0.04 | 1.3 | 6.9 | 32.5 |
| $S_a\Big]_{10}^{90}$ cc | 14.6 | 10.8 | 6.1 | |
| $S_d\Big]_{10}^{90}$ cc | 8.0 | 8.3 | 14.5 | >30 |
| SiO₂ | 60.6 | 60.9 | 60.7 | 59.0 |
| Al₂O₃ | 19.6 | 18.6 | 18.7 | 18.0 |

TABLE 2-continued

PULSE TEST RESULTS FOR Ba—K—Y FAUJASITES AT VARIOUS Ba/K RATIOS

| Example I | 1A | 1B | 1C | 1D |
|---|---|---|---|---|
| $K_2O$ | 8.8 | 8.6 | 6.9 | 2.2 |
| BaO | 9.1 | 10.0 | 11.0 | 18.5 |
| $Na_2O$ | 0.72 | 0.53 | 0.68 | 0.58 |
| Molar $BaO/K_2O$ | 0.63 | 0.71 | 0.98 | 5.17 |

EXAMPLE II

Example IC was repeated except that the temperature was lowered to 125° C. The results were very little affected as can be seen by the following Table 3.

TABLE 3

| B p/e | 3.37 |
|---|---|
| B p/m | 4.21 |
| B p/o | 3.70 |
| $\Delta$ W cc | 7.6 |
| n-$C_9$ H.W. cc | 12.00 |
| p-xylene Ret. Vol. cc | 34.0 |
| Molar $BaO/K_2O$ | 0.98 |

The adsorbent, Ba-K-Y, and the desorbent, 30% m-DFB in n-$C_7$, were the same as in Example IC.

EXAMPLE III

Another pulse test was run under the same conditions and with the same materials as Example I, except that the $BaO/K_2O$ molar ratio was 1.2. The desorbent was 30% m-DFB (b.p. 82° C.) mixed with normal heptane (n-$C_7$). The selectivities (B) for the xylene isomers were as follows:

$B\,p/eb = 3.02$
$B\,p/m = 3.94$
$B\,p/o = 3.00$ $$S_a\Big]_{10}^{90} = 11.7\ cc\quad S_d\Big]_{10}^{90} = 16.7\ cc$$

The p-xylene retention volume was 22.8, indicating a satisfactory desorption time. The width of the n-$C_9$ peak at half height was 11.9 cc. The $\Delta W$ (as defined hereinabove) was 1.1 cc. The adsorbent composition was:

| Wt. % $SiO_2$ | 60.6 |
|---|---|
| Wt. % $Al_2O_3$ | 19.1 |
| Wt. % BaO | 13.1 |
| Wt. % $K_2O$ | 6.7 |
| Wt. % $Na_2O$ | 0.6 |
| $BaO/K_2O$ (molar) | 1.2 |

The results are also illustrated by the chromatogram in FIG. 2 showing that p-xylene can be separated from other isomers where the $BaO/K_2O$ molar ratio is 1.2.

EXAMPLE IV

The pulse test of Example III was repeated except that the desorbent used was 100% fluorobenzene (b.p. 85° C.). The selectivities (B) for the xylene isomers were:
 B p/eb=2.25
 B p/pm=2.80
 B p/o=3.50

Figure 3:
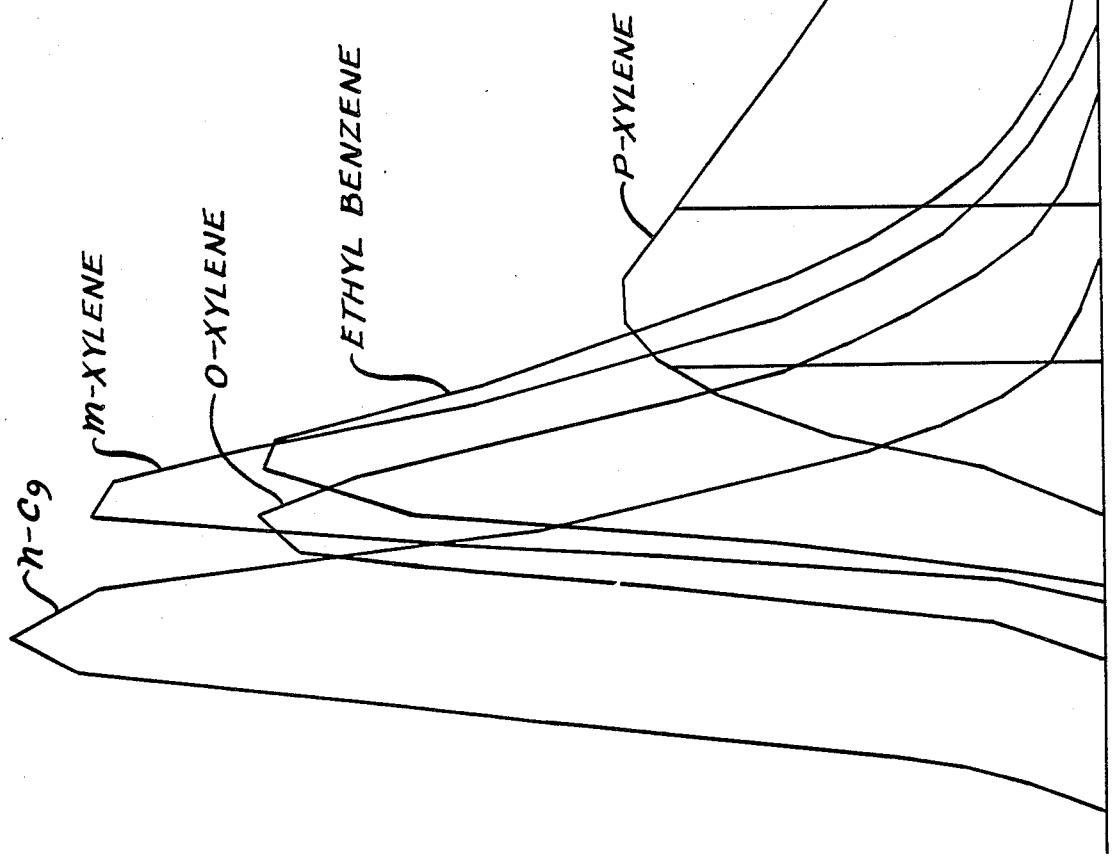
FIG. 3 is similar to FIG. 1A except that the molar ratio of BaO to $K_2O$ is 1.2 and the desorbent is fluorobenzene.

The para-xylene retention volume as 25.7 cc. The width of the n-$C_7$ peak at half height was 12.3 cc. The $\Delta W$ cc (as defined above) was 18.3 cc. The molar $BaO/K_2O$ ratio is 1.2. The breakthrough slope, $$S_a\Big]_{10}^{90},$$

is 7.9 cc. The desorption slope, $$S_d\Big]_{10}^{90},$$

is 46.4 cc. The results of the pulse test are shown in the chromatogram of FIG. 3. While the selectivities obtained herein approximated those obtained using toluene as a desorbent, fluorobenzene has the same advantage as the other fluorobenzenes disclosed herein, namely a lower boiling point, whereby the recovery of desorbent by distillation can be achieved.

EXAMPLE V

The pulse test of Example III was repeated except that the desorbent used was 30% m-DFB in n-$C_7$ and the BaK-Y zeolite had a molar $BaO/K_2O$ ratio of 1.05 and the following composition:

| Wt. % $SiO_2$ | 60.8 |
|---|---|
| Wt. % $Al_2O_3$ | 18.8 |
| Wt. % BaO | 11.8 |
| Wt. % $K_2O$ | 6.9 |
| Wt. % $Na_2O$ | 0.63 |

The selectivities (B) for the xylene isomers were:
 B p/eb=2.72
 B p/m=3.85
 B p/o=3.40

The p-xylene retention volume was 39.6 cc. The width of the n-$C_7$ peak at half height was 10.1 cc. The $\Delta W$ (as defined previously) was 6.71 cc. The results are shown in the chromatograph of FIG. 4.

EXAMPLE VI

The pulse test of Example III was repeated except that the desorbent was 30% ortho-difluorobenzene in 70% n-$C_7$. The $BaO/K_2O$ molar ratio was 1.05. The selectivities (B) for the xylene isomers were as high as those for meta-difluorobenzene:
 B p/eb=2.4
 B p/m=3.23
 B p/o=4.45

The p-xylene retention volume was 32.2, indicating a moderate desorption time. The width of the n-$C_7$ peak envelope at half height was 10.1 cc. The $\Delta W$ (as defined hereinabove) was 9.7 cc.

EXAMPLE VII

The pulse test of Example III was repeated except that the molar $BaO/K_2O$ ratio was 1.13 and that 30 vol. % m-DFB was run for Example VIIA and 100 vol. % m-DFB for Example VIIB. FIGS. 5A and 5B and Table 4 illustrate the finding that at constant $BaO/K_2O$ ratio, the selectivity (B) is enhanced when the concentration of the m-DFB is increased from 30% to 100%.

TABLE 4

| Example | VIIA | VIIB |
|---|---|---|
| Molar BaO/K₂O ratio | 1.13 | 1.13 |
| Desorbent | 30 vol. % m-DFB | 100 vol. % m-DFB |
| B p/e | 2.50 | 3.95 |
| B p/m | 3.63 | 4.46 |
| B p/o | 3.21 | 3.82 |
| p-Xylene Ret. Vol. | 47.89 cc | 17.97 cc |
| W | 10.84 cc | −0.7 cc |
| n-C₉ H.W. | 9.64 cc | 11.8 cc |
| $S_a \rbrack_{10}^{90}$ | 9.32 cc | 7.2 cc |
| $S_d \rbrack_{10}^{90}$ | 14.5 cc | 7.2 cc |

EXAMPLE VIII

Figure 6B:
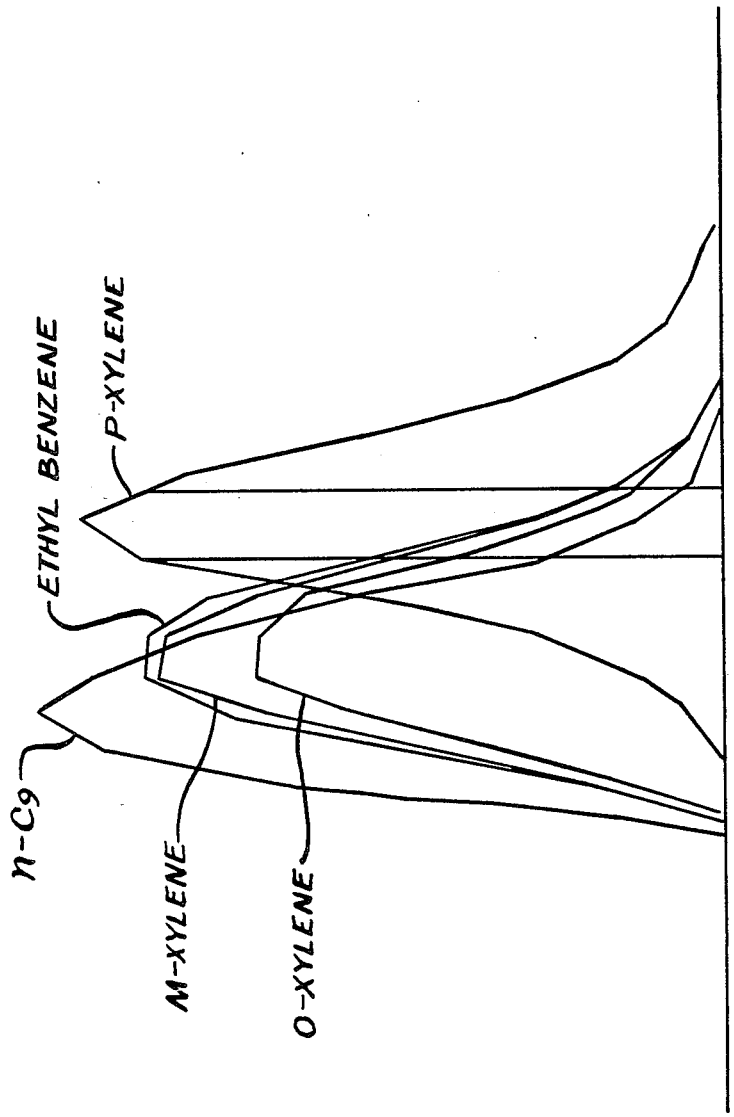

The pulse test of Example VII was repeated except that the molar BaO/K₂O ratio was 0.99. The results are illustrated by FIGS. 6A and 6B and Table 5 below. Meta-xylene contained in the feed is recovered before the ethylbenzene fraction is removed in FIG. 6A, but m-xylene cannot be separated from ethylbenzene and/or o-xylene in FIG. 6B and are recovered together. It is noted, comparing the results of FIG. 6A with FIG. 5A of Example VII and of 6B with 5B, that with increased BaO/K₂O ratio, the desorption strength of the m-DFB, as manifest in the p-xylene retention volume (Ret. Vol.), decreases. For example, the retention volume is 37.17 cc for a 0.99 ratio (Example VIIIA and FIG. 6A) and 47.89 cc for a 1.13 ratio (Example VII and FIG. 5A) both at 30% m-DFB. Likewise, for a retention volume of 11.44 cc and a 0.99 ratio at 100% m-DFB, the retention volume increases to 17.97 cc at 1.13 molar ratio. Furthermore, the selectivity (B) of the adsorbent for p-xylene with respect to the desorbent is greater than one and, therefore, is favorable:

$$B = S_d \rbrack_{10}^{90} cc / S_a \rbrack_{10}^{90} cc = \frac{10.1}{8.6} = 1.17$$

TABLE 5

| Example | VIIIA | VIIIB |
|---|---|---|
| Molar BaO/K₂O ratio | 0.99 | 0.99 |
| Desorbent | 30 vol. % m-DFB | 100 vol. % m-DFB |
| B p/e | 2.86 | 3.84 |
| B p/m | 3.77 | 4.18 |
| B p/o | 3.44 | 3.94 |
| p-Xylene Ret. Vol. | 37.17 cc | 11.44 cc |
| ΔW | 6.02 cc | −2.39 cc |
| n-C₉ H.W. 9.91 cc | 13.05 cc | |
| $S_a \rbrack_{10}^{90}$ | 9.05 cc | 8.6 cc |
| $S_d \rbrack_{10}^{90}$ | 12.3 cc | 10.1 cc |

EXAMPLE IX

In a pulse test, as described above, another feed was used to determine the ability of the barium-potassium exchanged Y faujasite to separate para-diethylbenzene (p-deb) from a mixture with meta-diethylbenezene (m-deb) and ortho-diethylbenzene (o-deb). The BaK-Y adsorbent had a molar BaO/K₂O ratio of 0.99. The same clay binder of Example I was used. The other variables were substantially like Example I. The desorbent was 30% m-difluorobenzene in n-heptane. The selectivity (B), with respect to the desorbent, is 1.09. The results are shown in Table 6, following, and FIG. 7.

TABLE 6

| Molar BaO/K₂O ratio | 0.99 |
|---|---|
| Desorbent | 30% m-DFB in N—C₇ |
| B p/m | 2.30 |
| B p/o | 3.78 |
| p-DEB Ret. Vol. | 43.27 cc |
| n-C₉ HW | 9.72 cc |
| $S_a \rbrack_{10}^{90}$ | 11.7 cc |
| $S_d \rbrack_{10}^{90}$ | 12.7 cc |
| B | 1.09 |

What is claimed is:

1. A process for separating the para-isomers of a dialkyl-substituted aromatic hydrocarbon from a mixture of said para-isomer and at least one other isomer of said aromatic hydrocarbon which process comprises contacting said mixture with a crystalline aluminosilicate adsorbent containing barium and potassium at exchangeable cationic sites within the adsorbent crystalline structure in a BaO/K₂O molar ratio of from about 0.6 to 1.2 at adsorption conditions selected to effect the adsorption of said para-isomer by said adsorbent and subsequently contacting said adsorbent with a desorbent material comprising a difluorobenzene selected from the group consisting of meta-difluorobenzene and ortho-difluorobenzene and mixtures thereof at desorption conditions to effect the removal of said para-isomer from said adsorbent and recovering from said adsorbent a stream concentrated in said para-isomer.

2. The process of claim 1 wherein said adsorbent is a type X zeolite.

3. The process of claim 1 wherein said adsorbent is a type Y zeolite.

4. The process of claim 1 wherein said desorbent comprises meta-difluorobenzene.

5. The process of claim 1 wherein said desorbent comprises ortho-difluorobenzene.

6. A process for separating para-xylene from a feed mixture comprising para-xylene and at least one other xylene isomer or ethylbenzene, which process comprises contacting, at adsorption conditions, said feed mixture with an adsorbent comprising an X- or Y-type zeolite having barium and potassium cations at exchangeable cationic sites which selectively adsorbs said para-xylene, and recovering said para-xylene by desorption at desorption conditions with a desorbent material comprising a difluorobenzene selected from the group consisting of meta-difluorobenzene, ortho-difluorobenzene and mixtures thereof.

7. The process of claim 6 wherein said adsorption and desorption conditions include a temperature within the range of from about 20° to about 250° C. and a pressure sufficient to maintain liquid phase.

8. The process of claim 6 wherein said process is effected with a simulated moving bed flow system.

9. The process of claim 8 wherein said simulated moving bed flow system is of the countercurrent type.

10. The process of claim 8 wherein said simulated moving bed flow system is of the countercurrent type.

11. The process of claim 6 wherein said adsorbent includes an amorphous inorganic oxide matrix.

12. The process of claim 6 wherein said desorbent is metadifluorobenzene.

13. The process of claim 6 wherein said barium and potassium cations are in a $BaO/K_2O$ molar ratio of from about 0.6 to about 1.2.

14. The process of claim 13 wherein the $BaO/K_2O$ molar ratio is from 0.9 to 1.1.

15. In an improved process for the separation of para-xylene from a feed containing a mixture of $C_8$ aromatic hydrocarbons, which process employs a crystalline aluminosilicate adsorbent selected from the group consisting of type X and type Y structured zeolites containing barium and potassium cations at the exchangeable cationic sites within said zeolite, said process comprising the steps of:
   i. contacting said adsorbent with said hydrocarbon feed at adsorption conditions to effect the selective adsorption of para-xylene by the adsorbent while simultaneously removing a raffinate material from the adsorbent which comprises the less selectively adsorbent components of the feed,
   ii. contacting said adsorbent with a desorbent material at desorption conditions to effect the displacing of said paraxylene from said adsorbent while simultaneously removing extract material from said adsorbent comprising desorbent and para-xylene; the improvement which comprises employing a desorbent material containing a difluorobenzene selected from the group consisting of meta-difluorobenzene, ortho-difluorobenzene and mixtures thereof.

16. The improved process of claim 14 wherein said adsorbent is a Y-type zeolite and contains barium and potassium cations in the $BaO/K_2O$ molar ratio of from 0.6 to 1.2.

17. The process of claim 15 wherein said desorbent material is meta-difluorobenzene.

18. The process of claim 1 wherein said dialkyl-substituted aromatic hydrocarbon para-isomer is p-diethylbenzene.

19. The process of claim 1 wherein said dialkyl-substituted aromatic hydrocarbon para-isomer is p-xylene.

* * * * *